United States Patent [19]

MacFarlane et al.

[11] Patent Number: 4,824,997
[45] Date of Patent: Apr. 25, 1989

[54] METHOD FOR PREPARATION OF ALKYL GLYCOLATES

[75] Inventors: Alistair MacFarlane, Woodlands, Tex.; David R. Dyroff; Robert V. Brill, both of St. Louis, Mo.

[73] Assignee: Monsanto Company, St. Louis, Mo.

[21] Appl. No.: 148,248

[22] Filed: Jan. 25, 1988

[51] Int. Cl.$^4$ .............................................. C07C 69/66
[52] U.S. Cl. ..................... 560/179; 562/518
[58] Field of Search ......................... 562/518; 560/179

[56] References Cited

U.S. PATENT DOCUMENTS

| | | | |
|---|---|---|---|
| 2,152,852 | 4/1939 | Loder | 562/518 |
| 3,754,028 | 8/1973 | Lapporte et al. | 562/518 |
| 3,911,003 | 10/1975 | Suzuki | 562/518 |
| 3,948,986 | 4/1976 | Suzuki | 562/518 |
| 4,016,208 | 4/1977 | Suzuki | 562/518 |
| 4,052,452 | 10/1977 | Scardigno et al. | 562/518 |
| 4,136,112 | 1/1979 | Bakshi | 562/518 |
| 4,431,486 | 2/1984 | Balmat | 203/69 |

FOREIGN PATENT DOCUMENTS 3133353 10/1983 Fed. Rep. of Germany ...... 562/518

52-71417 6/1977 Japan .............................. 562/518

Primary Examiner—Bruce D. Gray
Attorney, Agent, or Firm—R. C. Loyer; A. E. Hoffman; A. H. Cole

[57] ABSTRACT

A method of carbonylation of formaldehyde is disclosed. In the method, an aqueous formaldehyde concentrate comprising between about 60% by weight and about 85% by weight formaldehyde, carbon monoxide and sulfuric acid are brought together in the absence of an effective amount of added Group IB cocatalyst in a reaction zone under a carbon monoxide partial pressure in the reaction zone of not greater than about $1.72 \times 10^7$ N/M$^2$. A carbonylation reaction is thereby effected in which a carbonylation product is produced comprising at least about 2% by weight sulfuric acid and a mixture of compounds of the formula:

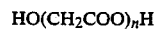

HO(CH$_2$COO)$_n$H wherein n is a positive integer of at least 1. Also disclosed is a method for preparation of an alkyl glycolate by esterification of the carbonylation reaction mixture.

28 Claims, No Drawings

METHOD FOR PREPARATION OF ALKYL GLYCOLATES

BACKGROUND OF THE INVENTION

This invention relates to the manufacture of alkyl glycolates, and more particularly to a novel method for preparation of glycolic acid and higher polyglycolides from formaldehyde.

Conventionally, alkyl glycolates have been prepared by esterification of glycolic acid. Glycolic acid, also called hydroxyacetic acid, is a commercially available industrial composition which has a variety of other uses, and typically is produced by highpressure carbonylation of formaldehyde. However, since glycolic acid as produced by such methods is very costly, the conventional process utilizing such commercially available glycolic acid in preparation of alkyl glycolates is relatively expensive.

Conventionally, glycolic acid is produced by carbonylation of a 37% or 50% by weight aqueous formaldehyde solution in the presence of an acid catalyst, usually sulfuric acid, under high ($4.14 \times 10^7$ to $6.9 \times 10^7$ N/M$^2$) pressure carbon monoxide (at gauge, CO partial pressure) and at a temperature of about 180° to 225° C. Glycolic acid is thereby produced according to the reaction.

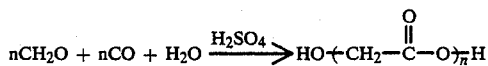

wherein n is a positive integer of at least 1.

This method for preparing glycolic acid is relatively expensive for a number of reasons. Thus, high capital costs are necessarily incurred in providing reactors designed to withstand the high reaction pressure. Because the reactants used in the process are very corrosive at the temperatures employed, expensive alloys are required for construction of process equipment, and this adds to the capital cost. The conventional method of removing the sulfuric acid catalyst from the glycolic acid reaction solution contributes significantly to operating costs. Since sulfate salts are highly soluble in aqueous glycolic acid solution, sulfuric acid cannot be efficiently removed from such solution by simple neutralization and filtration techniques. Instead it has been found necessary to remove the sulfuric acid by ion exchange, which tends to be costly.

Because removal of sulfuric acid is expensive and difficult, it has been considered desirable to maintain the concentration of sulfuric acid catalyst in the reaction mixture relatively low. However, it has been found that the lower the sulfuric acid concentration, the higher the pressure and temperature required for an acceptable reaction rate. Benefits achieved in reducing sulfuric acid are to some degree offset by higher capital cost for the reactor.

Moreover, in the standard method for preparing glycolic acid, undesirable side reactions compete with the carbonylation reaction, lowering the selectivity of the carbonylation reaction. Undesirable side reactions inherent in the conventional methods for preparing glycolic acid include the Cannizzaro reaction, conversion of methanol to methoxyacetic acid, and diglycolic acid formation. In the Cannizzaro reaction, formaldehyde reacts with water to form methanol and formic acid.

Various techniques are known for reducing the problems encountered in preparing glycolic acid from formaldehyde. However, these methods have met with little success. For example, the reaction has been run with low concentrations of water by using solid paraformaldehyde, but paraformaldehyde is very expensive and, since it is solid, it does not readily lend itself to production usage involving pumping and the like. Commercially available formaldehyde solutions of lower water content, such as 50% formaldehyde solutions, have also been tested without fully satisfactory results. For example, as shown in U.S. Pat. No. 4,431,486, 56.2% formaldehyde has been used, but carbon monoxide pressure of $4.14 \times 10^7$ to $6.9 \times 10^7$ N/M$^2$ and a temperature of 220° C. have still been necessary to produce an 85% yield within an acceptable reaction time. Higher temperatures also have been tried, but the higher temperatures increase the corrosivity of the reactant mixture as well as undesirable side reactions.

Salts of monovalent Group IB metal ions ($CU^I$, $AG^I$, $AU^I$) have been used with sulfuric acid to effect carbonylation reactions at lower pressures, but such systems suffer severe disadvantages such as extreme sensitivity to catalyst poisoning by water, the lack of practical methods for separation and recycle of the metallic catalyst, restriction to temperatures not exceeding about 60° C., and restriction to final reaction mixtures in which the polyglycolide content of the liquid phase does not exceed about 60% by weight. See Japan Kokai Pat. No. SH057(1982)-46934, 3/17/82 and Y. Souma & H. Sano, Nippon Kagaku Kaishi 2, 263 (1982).

Other processes for preparing glycolic acid or higher polyglycolides, as described in U.S. Pat. Nos. 3,911,003; 4,016,208; and 4,136,112 use hydrogen fluoride as the acid catalyst. However, since hydrogen fluoride is extremely corrosive, these processes involve elaborate equipment and handling procedures.

In short, it has been the general experience in the art that attempts to solve one of the problems inherent in the standard method for preparation of glycolic acid have exacerbated the other problems.

SUMMARY OF THE INVENTION

Briefly, one aspect of the present invention is directed to a method for preparation of polyglycolide by carbonylation of formaldehyde. In the method of this invention, an aqueous formaldehyde concentrate comprising from about 60% to about 85% by weight formaldehyde, carbon monoxide and a catalytic amount of sulfuric acid are brought together in the absence of an effective amount of added Group IB cocatalyst in a reaction zone under a carbon monoxide partial pressure in the reaction zone of not greater than about $1.72 \times 10^7$ N/M$^2$. A carbonylation product is produced comprising polyglycolide and at least about 2% by weight sulfuric acid.

The term "polyglycolide", referring to the reaction product of the process of this invention means herein a mixture comprising compounds represented by the formula HO(CH$_2$COO)$_n$H wherein n is a positive integer of at least 1.

In another aspect of this invention the carbonylation product is esterified without prior removal of the sulfuric acid to form an esterification product comprising an alkyl glycolate of the form

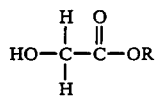

where R is a lower alkyl group such as methyl, ethyl, n-propyl, isopropyl, n-butyl, isobutyl, and the like. The alkyl glycolate is then separated from the esterification reaction mixture.

The present invention is further directed to a method for preparation of an alkyl glycolate comprising carbonylation of formaldehyde in the presence of sulfuric acid and in the absence of an effective amount of added Group IB cocatalyst at a carbon monoxide partial pressure (gauge) not greater than about $1.72 \times 10^7$ N/M² to form a final carbonylation reaction mixture comprising polyglycolide and at least about 2% by weight sulfuric acid. Next an alcohol of the form ROH, where R is a lower alkyl group such as methyl, ethyl, n-propyl, isopropyl, n-butyl, and the like, is mixed with the carbonylation reaction mixture to effect an esterification reaction and form an esterification product comprising an alkyl glycolate of the form

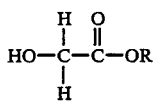

where R is lower alkyl. Then, the alkyl glycolate is separated from the esterification reaction mixture.

DETAILED DESCRIPTION OF THE PREFERRED EMBODIMENTS

In accordance with this invention, a process has been discovered in which polyglycolide can be prepared economically at commercially acceptable conversion rates using moderate pressure and relatively low sulfuric acid concentration for the carbonylation of formaldehyde. In the method, an aqueous formaldehyde concentrate comprising at least 60% by weight formaldehyde, carbon monoxide and a sulfuric acid catalyst are brought together in the absence of an effective amount of added Group IB cocatalyst in a reaction zone at moderate pressure conditions, thereby effecting within for example about twenty hours, preferably within two to ten hours, a high conversion to polyglycolide. Optionally, the polyglycolide contained in the carbonylation reaction mixture is then esterified to form an esterification product comprising an alkyl glycolate, which then is separated from the esterification reaction mixture.

Surprisingly, it has been found that by using a moderately high concentration of sulfuric acid while maintaining a low water concentration, which can be achieved by using a formaldehyde concentrate having a formaldehyde concentration of between about 60% by weight and about 85% by weight, a product appropriate for esterification to an alkyl glycolate may be produced economically at carbon monoxide partial pressures, and total pressures, much lower than the conventional $4.14 \times 10^7$ N/M² to $6.9 \times 10^7$ N/M². With a concentration of sulfuric acid catalyst in the carbonylation reaction mixture only slightly higher than is employed in the standard methods, the conversion and selectivity achieved are at least as good as, and typically better than, those achieved by the conventional process. Further, it has been found that the temperature of the reaction mixture need not be greater than that of the prior art processes, and can even be somewhat lower.

In addition, the carbonylation step of the subject process is particularly adapted for incorporation in an overall synthesis of an alkyl glycolate, the next step in which, i.e., esterification, has been found to suffer no significant adverse effect from the amount of sulfuric acid catalyst remaining from the carbonylation reaction. It has been found that the presence of this increased amount of acid catalyst increases the rate of esterification to a very high degree. Thus, the acid catalyst need not be removed by expensive ion exchange techniques before esterification. After esterification, the acid catalyst can be removed relatively easily by adding a base to neutralize the acid, thereby forming a salt which is partly insoluble in the alkyl glycolate solution, and filtering the insoluble salt from the alkyl glycolate solution. Accordingly, the present invention results in substantial monetary savings not only by substantially reducing the pressure under which carbonylation takes place, but also by avoiding the costly techniques previously employed for removing acid catalyst from glycolic acid solution prior to esterification.

The formaldehyde concentrate used in the carbonylation reaction should comprise at least about 60% by weight formaldehyde, and preferably between about 70% and about 85%, and more preferably between about 70% and about 80%, by weight formaldehyde. Optimal results in the carbonylation reaction have been found to occur with a formaldehyde concentration of between about 70% and about 77% by weight formaldehyde. In order to minimize unwanted side reactions, the methanol content of the concentrate used as feed in the carbonylation reaction should be less than about 2% by weight, preferably less than about 1%.

As used herein, the term "formaldehyde concentrate" means an aqueous solution substantially free of undissolved formaldehyde and comprising dissolved formaldehyde in any one of its various forms including $CH_2O$, trioxane, $HO(CH_2O)_nH$ where n is at least 1, or mixtures thereof, irrespective of the method by which said aqueous solution was produced. Where the formaldehyde content of such a concentrate is specified as a weight percentage, this refers to the weight percentage of $CH_2O$ which would result if all forms of formaldehyde present were converted to the equivalent amount of $CH_2O$ without changing the total weight of the concentrate.

A convenient laboratory method for preparing a formaldehyde concentrate of a given strength is to melt trioxane in an oven at 75° C., filter the molten material through several layers of cheese cloth to remove insoluble paraformaldehyde, and mix the filtrate with the appropriate amount of hot water. Small amounts of methanol can also be mixed in if desired. The resulting solution is then stored at 70°-85° C. until used, preferably for a period not exceeding about five days.

For commercial operations in accordance with this invention it is preferred that the formaldehyde concentrate be derived from formaldehyde sources other than trioxane or solid paraformaldehyde, because of the relatively high cost of these two sources. Preferred formaldehyde sources include commercially available aqueous solutions such as those containing about 37% or 50% formaldehyde and gaseous mixtures rich in formaldehyde such as those produced during formaldehyde manufacture. Mixtures of formaldehyde with low methanol content are particularly preferred, i.e. about 1.0% by weight methanol or less.

Numerous methods are known in the art for the conversion of commercial formaldehyde solutions or gaseous mixtures to formaldehyde concentrates of the strengths required for the process of this invention. For example, in U.S. Pat. No. 3,493,472, a method is taught wherein a gaseous reaction mixture comprising formaldehyde is fed to the central portion of a heated distillation column operated at a pressure less than atmospheric pressure. A fraction lower in formaldehyde content is removed at the top and collected by condensation and absorption, with part of the resulting liquid being returned to the top of the column as reflux. At the bottom of the column a highly concentrated formaldehyde solution is drawn off. It is taught that formaldehyde solutions having a concentration in excess of 67 percent and as high as 96 weight percent formaldehyde can be thus produced in a single step without further refining.

In U.S. Pat. Nos. 2,527,654 and 2,527,655 methods are taught wherein an aqueous formaldehyde solution containing 25-50 weight percent formaldehyde is fed to a distillation column or combination of distillation columns and separated to produce a formaldehyde concentrate containing 70-97% formaldehyde. The concentrate is withdrawn from the bottom of a column and a weak formaldehyde solution containing less than about 10% formaldehyde is withdrawn from the top of a column operating with a pressure below atmospheric pressure (preferably 500 mm Hg absolute or lower) at the top. Optionally the weak formaldehyde solution may be further distilled at higher pressure to recover most of the contained formaldehyde for recycle.

In French Pat. No. 1,546,309 and Belgium Pat. No. 764393 methods are taught wherein an aqueous formaldehyde solution is fed to a low residence time evaporator (or a series of such evaporators) operated at pressures below one atmosphere. This operation thereby fractionates formaldehyde into a vapor fraction with a formaldehyde concentration (by weight) less than that of the feed and a bottom fraction consisting of a formaldehyde concentrate containing up to about 85 weight % formaldehyde. In one case, the evaporator is a vertical tube with a heating jacket and a rotating feeding device near the top which distributes the feed evenly over the inner wall of the heated tube. The liquid residence time is typically about 2 minutes, and the jacket temperature is adjusted to obtain the desired degree of concentration. In another case, the evaporator is in the form of a rotating heated conical surface, with the feed distributed over the inner surface of the cone and the film thickness controlled partly by the centrifugal force resulting from the rotation. In this case the liquid residence time is less than one minute (generally not more than about 5-10 seconds) and the operating pressure is generally about 40-120 mm Hg. Using a feed containing 50.9% formaldehyde, at an absolute pressure of 129 mm Hg within the evaporator, a formaldehyde concentrate containing 79.22% formaldehyde was thus obtained in a single stage in one example, with 92.9% of the formaldehyde feed being recovered in the concentrate. Such a concentrate can be held for at least an hour or two at 80° C. without appreciable precipitation of solid paraformaldehyde. However, to minimize both paraformaldehyde precipitation and decomposition reactions such as the Cannizzaro reaction, it is preferred to perform the formaldehyde concentration step only shortly before the initiation of the carbonylation reaction.

To initiate carbonylation, the formaldehyde concentrate is preferably fed to a continuous stirred tank reactor (CSTR) along with sulfuric acid and carbon monoxide gas in a manner discussed below. The process of this invention may be conducted at moderate pressure and acid concentration. Consequently, the CSTR need not be constructed of extremely expensive, unusually strong and anticorrosive materials, but may be formed of any of a number of commonly available materials, such as Hastelloy B, or the reactor may be zirconium or silver lined.

The acid catalyst should be a strong acid, preferably sulfuric acid, although other strong acid catalysts, such as Nafion (a trade designation of E. I. du Pont De Nemours for a perfluorosulfonic acid membrane typically used as an ion-exchange resin) can be employed. Sulfuric acid is particularly desirable as it is readily available, can be introduced in liquid form without significant addition of water, and is less corrosive than hydrogen fluoride and far less expensive than Nafion. In fact, one of the particular advantages of the novel process of this invention is the high yields that are obtainable at reasonable pressures and reaction rates without the necessity of employing highly corrosive or expensive catalysts. Since the carbonylation reaction rate increases with higher carbon monoxide partial pressure while the reactor cost increases with overall pressure, the carbon monoxide gas should be of high carbon monoxide concentration.

With a sulfuric acid catalyst, the reactants may be introduced in proportions such that the sulfuric acid concentration in the final carbonylation product optimally is at least about 2% by weight. While levels much higher than 2% can be used, for example about 10%, and reaction rates increase at such higher levels, this results in rather high costs for the sulfuric acid, product neutralization and separation, waste disposal, etc. Thus, it is preferred that the concentration of sulfuric acid in the final carbonylation product be between about 2% by weight and about 4% by weight. This sulfuric acid level is only slightly greater than that typically employed in high pressure carbonyation reactions. The partial pressure of carbon monoxide is maintained below about $1.72 \times 10^7$ N/M$^2$, preferably $5.5 \times 10^6$ to $1.38 \times 10^7$ N/M$^2$.

The carbonylation reaction is exothermic, allowing the desired reaction temperature of 150° C. to 180° C. to be maintained without heating the mixture externally. The mixture is highly agitated to ensure a high degree of contact between the liquid and gas reactants. The agitation is continued throughout a residence time of about 2 to 20 hours for a continuous process, preferably about 2-10 hours. For the process to be commercially practical, the formaldehyde conversion should be at least about 90 percent, and preferably at least 95 percent. The selectivity to polyglycolide should be at least about 80, and preferably at least 85 percent. Since the kinetics of the reaction dictate that the rate decreases as the reaction progresses, it is understood that for commercially practical productivity and selectivity to be achieved, a formaldehyde conversion of at least about 90 percent should occur in an eight hour residence time. In accordance with this invention, it has been found that up to 99 percent conversion of formaldehyde is effected within such residence time, with up to a 92 percent selectivity to polyglycolide. Such conversion and selectivity result in up to about a 91 percent recovered yield of polyglycolide. It is preferred to select conditions such that the yield of polyglycolide is at least 80%, more preferably at least about 85% based upon the amount of formaldehyde added.

The carbonylation reaction of this invention may be run as either a continuous process or a batch process. For many commercial applications, the continuous process should be more practical because it allows relatively high flow rates with moderately sized reactors. In a batch reaction it is desirable to initiate the reaction with a substantial heel of converted material to reduce the average formaldehyde concentration and thereby suppress the Cannizzaro reaction. For the continuous process, it has been found desirable to employ more than one stage to reduce the size of the reactors needed.

In a continuous carbonylation process of two or more stages, the CSTRs of the initial stage should be large enough to ensure high enough conversion of formaldehyde (about 85 percent to about 97 percent) to suppress the Cannizzaro reaction. Preferably, the conversion resulting from the first stage exceeds about 94 percent. Below 94 percent, the ultimate yield of polyglycolide is lower, but productivity is greater so that the reactors needed may be smaller and so less expensive. The initial stage may comprise one relatively large CSTR, or two or more CSTRs running in parallel. If two or more CSTRs are run in parallel, the various feed streams should be distributed between the reactors such that the concentration of sulfuric acid is substantially the same in each reactor and the carbon monoxide partial pressure is between about $5.5 \times 10^6$ N/M$^2$ and about $1.72 \times 10^7$ N/M$^2$ in each reactor. The agitation in the reactor(s) should be intense to ensure extensive contact of the gas and liquid. Preferably the agitation intensity should be high enough so that a further increase in the intensity of the agitation would not influence the reaction significantly. The exact size of the reactor(s) depends on the desired flow rate and the desired conversion as discussed above.

Preferably the liquid product of the first stage is transferred to a finishing stage, comprising one or more CSTRs. If two or more CSTRs were employed in the first stage, the product streams may be combined and introduced to a single finishing stage CSTR. Carbon monoxide is introduced to the finishing stage CSTR to maintain between about $5.5 \times 10^6$ N/M$^2$ and about $1.72 \times 10^7$ N/M$^2$ of carbon monoxide partial pressure in the finishing stage CSTR. As with the first stage reactor(s), the finishing stage reactor is intensely agitated. The finishing stage thereby results preferably in an ultimate formaldehyde conversion of at least about 97 percent, and more preferably about 98 to about 99 percent. The overall yield, as measured by moles of desired product (polyglycolide) to moles of formaldehyde, typically exceeds 85%.

After separation of excess carbon monoxide, the carbonylation reaction mixture thus formed comprises polyglycolide, water, acid catalyst, and relatively minor amounts of unconverted formaldehyde and side reaction products. The average chain length of the polyglycolide can vary widely, but to facilitate the preparation of alkyl glycolates by esterification of the carbonylation product, it is preferred that the average chain length of the polyglycolide (calculated on the basis of zero free water content) be less than about four, more preferably not greater than about two.

In the preferred method of preparing alkyl glycolate, an excess of alcohol, typically at least about a 50% molar excess, and more preferably about a 100% molar excess, of the formula ROH, where R is a lower alkyl group such as methyl, ethyl, n-propyl, isopropyl, n-butyl, isobutyl, and the like, is employed. The alcohol is mixed with the carbonylation reaction mixture for esterification of the polyglycolide in the carbonylation mixture. In one preferred embodiment, the alcohol is methanol, and the methanol is added in about a 2:1 molar ratio (generally between about 1.5:1 and about 2.5:1) to the polyglycolide. The presence of the acid catalyst from the carbonylation reaction results in a rapid esterification reaction.

When esterifying with methanol, the methanol and the carbonylation product may be introduced into an esterification reactor in a methanol/polyglycolide mole ratio of about 2:1. The reactants are maintained at a temperature of between about 65° C. and about 125° C. Under these conditions, at least 75% conversion by esterification has been found to take place relatively rapidly, i.e., within about five minutes to about three hours.

The resulting esterification reaction mixture comprises methyl glycolate, excess methanol, unconverted polyglycolide, acid catalyst and water.

The sulfuric acid catalyst may be substantially eliminated from the esterification product by addition of a sufficient amount of a suitable base such as a commercial 50% sodium hydroxide solution to raise the pH of the mixture to about 2.5 followed by filtration. Thus, addition of sodium hydroxide produces a sulfate salt which is at least partially insoluble in the methyl glycolate solution, particularly in the presence of the excess methanol added for esterification. Accordingly, the insoluble sulfate can be removed by routine filtration methods.

The resulting solution is then fractionated, preferably by two continuous stages. For example, the filtered esterification product is pumped to a low residence time, relatively short distillation column operated at about atmospheric pressure to remove methanol and water overhead. The product from the bottom of this first stage is then pumped to a low residence time, low pressure (preferably about 100 mm Hg absolute) evaporator operated at between about 90° C. and about 250° C. to recover the methyl glycolate overhead. The second stage evaporator may be a falling-film or preferably a wiped film evaporator preferably equipped with a very short distillation column at the top. The bottom fraction produced by this stage, if desired, may be salvaged and recycled back to the esterification reactor. The residence time in both fractionation stages and the associated piping and equipment should be short in order to minimize such side reactions as ester hydrolysis and higher polyglycolide formation.

Recoveries exceeding 90% by weight of the alkyl glycolate formed have been achieved in this manner where the alkyl glycolate is methyl glycolate. When the alkyl group of the ester comprises a carbon chain of more than one carbon atom, the boiling points of the alcohol and the alkyl glycolate are higher. Thus, separation by distillation may become more difficult. In such cases where alkyl glycolate recovery by distillation is feasible, the required conditions can be determined by routine experimentation in view of the present disclosure.

The purity of methyl glycolate product thus derived from esterification and subsequent fractionation has been found to be as high as 96% by weight or more. On the other hand, the methanol and the water content have each been found to be less than 2% by weight of total product. Likewise, the concentration of other impurities does not exceed about 2 or 3% by weight. While a significant amount of water (more than several weight percent) tends to hydrolyze the ester with time, the small amounts of impurities found to be present in the product of the postesterification fractionation step do not adversely affect the product in any significant manner for at least several days. Of course, still higher methyl glycolate purity could be obtained if desired by redistillation of the initial product by any number of known methods.

The following examples illustrate the invention.

EXAMPLE 1

This example illustrates the conversion of a formaldehyde concentrate to polyglycolide in a continuous reactor in accordance with the present invention.

The reactor employed in all runs of this example was an autoclave constructed of Hastelloy-B2 metal with a working volume of about 705 ml. Feed streams entered continuously below the liquid surface, and the product was removed continuously by overflow to a pressurized receiver. The agitator was operated at 1750 RPM and an internal baffle was provided. In separate experiments it was shown that this degree of agitation was sufficient to minimize effects of mass transfer from the gas phase to the liquid phase. Temperature was controlled by means of external cooling coils and electrical heaters. A large excess (3.6–4.1 fold) of carbon monoxide (CP grade) was fed to ensure that carbon monoxide purity remained high within the reaction zone. The sulfuric acid employed was AR grade, 98% $H_2SO_4$. The formaldehyde concentrate employed in all runs of this example contained 70% $CH_2O$, 1.5% $CH_3OH$, and 28.5% $H_2O$. This concentrate was derived from trioxane and was held at 70°–85° C. prior to being fed to the reactor.

Operating conditions and results for a number of runs are summarized in Table I. Once any particular set of conditions had been established, operation was continued at those conditions long enough to displace the reactor contents at least three times prior to emptying the product receiver and beginning the collection of a representative product for analysis. The selectivities and yields reported are based upon the production of all forms of polyglycolide $(HO(CH_2COO)_nH)$. Selectivity is calculated based upon the amount of formaldehyde converted, while yield is based upon the amount of formaldehyde fed. In all runs, the principal by-products were methanol, formic acid, methoxyacetic acid and diglycolic acid or derivatives thereof. It can easily be seen that rather high conversions and selectivities can be obtained under a variety of conditions within the scope of this invention.

TABLE I

CONTINUOUS CARBONYLATION RUNS

| | Run No. 1 | 2 | 3 | 4 | 5 | 6 | 7 |
|---|---|---|---|---|---|---|---|
| Reaction Temp. °C. | 165 | 165 | 165 | 165 | 165 | 165 | 175 |
| Wt. % $H_2SO_4$ in Final Liquid Phase | 2.9 | 3.9 | 3.9 | 2.9 | 2.9 | 3.9 | 2.9 |
| Residence Time (Hours) | 6 | 6 | 6 | 10 | 10 | 10 | 6 |
| CO Pressure (N/M$^2$) | $8.3 \times 10^6$ | $5.5 \times 10^6$ | $8.3 \times 10^6$ | $5.5 \times 10^6$ | $8.3 \times 10^6$ | $8.3 \times 10^6$ | $8.3 \times 10^6$ |
| % Conversion of Formaldehyde | 93.4 | 94.1 | 96.3 | 95.4 | 96.5 | 97.4 | 97.0 |
| Selectivity | 89.4 | 87.7 | 90.7 | 89.0 | 92.1 | 91.6 | 90.8 |
| Yield | 83.5 | 82.5 | 87.3 | 84.9 | 88.9 | 89.2 | 88.0 |

EXAMPLE 2

This example illustrates the conversion of a formaldehyde concentrate to polyglycolide in a batch reactor in accordance with the present invention.

The reactor employed in all runs of this example was a 300 ml autoclave composed of Hastelloy C276 metal equipped to provide intense agitation. Run conditions and results are summarized in Table II. In each run, an initial reaction mixture was formed from a relatively small amount of a formaldehyde concentrate and $H_2SO_4$ and a relatively large amount of an already converted reaction product of corresponding composition (polyglycolide). Such a mixture corresponds in composition to a reaction mixture partially converted to polyglycolide. In Table II, the figures given for initial $CH_2O$ conversion define the conversion level to which the starting composition corresponds. The initial reaction mixture was then reacted with CO under the indicated conditions, resulting in an increase in conversion level. During the reaction period, no new reactants were added and no products were withdrawn. Thus, the reaction conditions given correspond to those in the later stages of a simple batch reaction. For a given set of conditions, this procedure was repeated many times with a portion of the reaction product from one cycle being used as the converted portion of the initial reaction mixture of the next cycle. Once the end of cycle composition was no longer changing significantly, no further cycles were run, and the final reaction product was analyzed to determine conversion and selectivity of the reaction. The results in Table II further illustrate the high conversions and selectivities which are obtained under widely varying carbonylation conditions within the scope of this invention.

TABLE II

BATCH CARBONYLATION RUNS

| | Run No. 8 | 9 | 10 | 11 | 12 | 13 | 14 | 15 | 16 | 17 |
|---|---|---|---|---|---|---|---|---|---|---|
| Reaction Temp. °C. | 160 | 160 | 150 | 170 | 160 | 150 | 180 | 160 | 160 | 160 |

TABLE II-continued

BATCH CARBONYLATION RUNS

| | Run No. | | | | | | | | | |
|---|---|---|---|---|---|---|---|---|---|---|
| | 8 | 9 | 10 | 11 | 12 | 13 | 14 | 15 | 16 | 17 |
| Wt. % $H_2SO_4$ in Final Liquid Phase | 3.9 | 3.9 | 2.0 | 3.9 | 3.0 | 3.9 | 2.5 | 3.9 | 2.5 | 3.9 |
| Residence Time (Hours) | 6 | 6 | 10 | 10 | 6 | 20 | 10 | 10 | 15 | 6 |
| CO Pressure ($N/M^2$) | $6.9 \times 10^6$ | $1.38 \times 10^7$ | $1.38 \times 10^7$ | $1.38 \times 10^7$ | $1.38 \times 10^7$ | $1.38 \times 10^7$ | $1.38 \times 10^7$ | $1.38 \times 10^7$ | $1.38 \times 10^7$ | $1.38 \times 10^7$ |
| % $CH_2O$ in $CH_2O$ Concentrate | 77 | 70 | 77 | 62.5 | 70 | 62.5 | 70 | 77 | 77 | 70 |
| Initial $CH_2O$ Conversion, % | 85 | 92 | 92 | 92 | 92 | 92 | 92 | 92 | 92 | 85 |
| Final $CH_2O$ Conversion, % | 95.5 | 97.4 | 96.3 | 95.9 | 96.5 | 96.2 | 99.3 | 98.1 | 97.8 | 96.6 |
| Selectivity (Based upon $CH_2O$) | 88.5 | 93.4 | 84.3 | 91.4 | 92.7 | 94.2 | 91.7 | 92.4 | 92.0 | 88.1 |

EXAMPLE 3

In the preceding examples the shortest carbonylation reaction time employed was six hours. This example illustrates results which are obtained in shorter carbonylation times in accordance with the present invention.

A

In a semicontinuous reactor (reactants fed and products withdrawn in small and frequent discrete increments) operated at 165° C. and $6.9 \times 10^6 \, N/M^2$ CO pressure, a 77% formaldehyde concentrate (derived from trioxane) was fed along with enough sulfuric acid to provide 3.9% $H_2SO_4$ in the final product. Residence time was four hours. Under these conditions, formaldehyde conversion was about 97% and selectivity (polyglycolide) was about 85%.

B

In a batch reactor provided with a heel of already converted material in an amount corresponding to an initial formaldehyde conversion of 85%, a 77% formaldehyde concentrate (derived from paraformaldehyde) was reacted with CO at $7.2 \times 10^6 \, N/M^2$ pressure and 160° C. The level of $H_2SO_4$ in the initial reaction mixture was 3.9% (corresponding to about 3.4–3.5% in the final reaction mixture). The reaction was terminated after 75 minutes. Analysis of the product indicated that the yield of polyglycolide from the formaldehyde charged was about 89.0%. Formaldehyde conversion was not determined separately. If conversion was less than 100%, then the reaction selectivity was correspondingly higher than 89%.

EXAMPLE 4

This example illustrates the preparation of an alkyl glycolate by reaction of an alcohol with a mixture comprising glycolic acid, higher polyglycolides, and between about 2 weight percent and about 4 weight percent sulfuric acid.

A carbonylation product was prepared as described herein from a formaldehyde concentrate containing 70% $CH_2O$. The estimated average polyglycolide chain length for such a product is about 1.4, where monomeric glycolic acid is treated as a polyglycolide of unit chain length and the level of free water is arbitrarily estimated to be nil. The sulfuric acid content of this carbonylation product was within the range 3.6–3.9 weight percent, formaldehyde conversion was about 95.5%, and selectivity to polyglycolide was about 87.4%. A mixture of 600.5 g of this carbonylation product and 481.6 g of methanol (about a two fold excess) was refluxed for three hours at atmospheric pressure. The resulting product was cooled to ambient temperature, neutralized to pH 2.5 with 50% NaOH, and filtered to remove precipitated sulfate. The filtrate was analyzed and found to contain 54.30% methyl glycolate, 10.01% glycolic acid, 24.32% methanol, 8.76% water, and about 2.61% miscellaneous impurities. Thus, under these conditions about 82 mole percent of the contained polyglycolide was converted to methyl glycolate in a single pass.

EXAMPLE 5

This example illustrates the production of methyl glycolate by conversion of a formaldehyde concentrate to a reaction mixture comprising polyglycolide and between about 2 weight percent and about 4 weight percent sulfuric acid, followed by esterification of this reaction mixture with methanol to form methyl glycolate which is then separated from the esterification mixture by neutralization of the sulfuric acid followed by distillation.

The neutralized esterification mixture of Example 4 was fed to a continuous 22 tray, one inch diameter Oldershaw distillation column operated at atmospheric pressure with the feed entering between trays 2 and 3, counting from the bottom. The reboiler was of the thermal siphon design and was sized to limit the residence time in the reboiler to about three minutes. The L/D (liquid returned to the column/total condensed distillate) was about ¼, the reboiler temperature was 155° C., the feed tray temperature was 113° C., and the temperature at the reflux splitter (top of the column) was 79° C. The resulting overhead fraction consisted mostly of methanol and water and contained only 1.96 weight percent methyl glycolate. The bottom fraction was pumped directly to the top of a continuous wiped film evaporator (Pope Scientific Company) with a wiped length of eight inches and an inside diameter of two inches. The temperature was 119° C. at the top of the evaporator and 203°–213° C. at the bottom. The bottom fraction from the evaporator was collected, and the vapor emerging from the top was sent to the bottom of a 2 tray Oldershaw distillation column operated at an L/D of ¼ and 104 mm pressure at the top. The temperature at the top of this column was about 90°–93° C. Since the top of the evaporator was piped directly into the bottom of this short column, the operating pressure of the evaporator, which was not directly measured, was only slightly higher than 104 mm. The overhead product from the two tray column consisted of about 97.1% methyl glycolate, 0.7% methanol, 1.6% water, and 0.6% other impurities. About 83.2% of the methyl glycolate contained in the neutralized esterification mixture was recovered in this overhead product.

About 216.9 g of the bottom fraction from the evaporator was mixed with 600.1 g of additional carbonylation product (same lot used above), and this mixture was esterified with methanol, neutralized to pH 2.5, and fractionated in substantially the same manner as described above. In the esterification step, conversion to methyl ester was about 80%, which is not substantially different from the 82% conversion obtained in the absence of recycled material. In the fractionation step, the temperatures in the evaporator were increased to 123°–128° C. at the top and 220°–225° C. at the bottom, and the pressure at the top of the two tray column was reduced to 95 mm Hg. The overhead product from the first column contained only 1.38% methyl glycolate. The overhead product from the two tray column consisted of about 97.7% methyl glycolate, 0.3% methanol, 0.7% water, and 1.3% other impurities. About 89.7% of the methyl glycolate contained in the neutralized esterification mixture was recovered in this overhead product.

About 203.3 g of evaporator bottom fraction generated as just described was mixed with 600.4 g of additional carbonylation product (same lot), and the above operations were again repeated except that L/D in the first column was increased to about 1/1, L/D in two tray column was reduced to about 1/7, and the temperature at the bottom of the evaporator was reduced to 212°–213° C. In this sequence, conversion in the esterification step was about 83% (vs 82% in the absence of recycled material), and the overhead product from the first column contained only 0.63% methyl glycolate. The overhead product from the two tray column consisted of about 96.2% methyl glycolate, 0.2% methanol, 0.8% water, and 2.8% other impurities. About 96.8% of the methyl glycolate in the neutralized esterification mixture was recovered in this overhead product.

In the final sequence, about 83% of the polyglycolide charged was converted to the methyl ester and about 96.8% of this ester was recovered as finished product. Thus, the single pass conversion of the glycolic acid values to recovered methyl ester was about 80%. Another 0.2% is accounted for as loss to the first column distillate. Analysis of the bottom fraction from the evaporator showed that the remaining glycolic acid values were contained in that fraction, within the accuracy of the analyses. Thus, in theory, by totally recycling all such bottom fractions in an ongoing series of esterification/separation operations, the recovery of glycolic acid values as purified methyl glycolate could be as high as 99.8%. In practice, the recovery would be somewhat lower due to the need to discard some of the evaporator bottom fraction in order to limit the build up of impurities in the recycle stream to an acceptable level.

As various changes could be made in the above constructions without departing from the scope of the invention, it is intended that all matter contained in the above description shall be interpreted as illustrative and not in a limiting sense.

What is claimed is:

1. A method comprising:
   bringing together in a reaction zone an aqueous formaldehyde concentrate comprising between about 60% by weight and about 85% by weight formaldehyde, carbon monoxide and a catalytic amount of sulfuric acid, in the absence of an effective amount of added Group IB cocatalyst, under a carbon monoxide partial pressure in said reaction zone of not greater than about $1.72 \times 10^7$ N/M$^2$ thereby effecting a carbonylation reaction in which a carboxylation product is produced comprising a mixture of compounds of the formula:

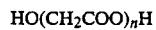
   HO(CH$_2$COO)$_n$H wherein n is an integer of at least 1 and in the range of from about 2% to about 10% by weight sulfuric acid.

2. A method as set forth in claim 1 wherein the formaldehyde conversion is at least about 90%.

3. A method as set forth in claim 2 wherein the selectivity to polyglycolide is at least about 85% based upon the formaldehyde converted.

4. A method as set forth in claim 1 wherein the concentration of formaldehyde in said aqueous formaldehyde concentrate is between about 70% by weight and about 80% by weight.

5. A method as set forth in claim 1 wherein the temperature in said reaction zone is between about 150° C. and about 180° C.

6. A method as set forth in claim 1 wherein the yield of polyglycolide is at least about 85 mole percent based on formaldehyde input.

7. A method as set forth in claim 1 wherein the reaction time is in the range of from about 2 to about 10 hours.

8. A method as set forth in claim 1 wherein the carbonylation reaction is a continuous process.

9. A method of claim 8 wherein the reaction time is within the range of from about 2 to about 20 hours.

10. A method of claim 1 wherein the pressure is in the range of from about $5.5 \times 10^6$ N/M$^2$ to about $1.38 \times 10^7$ N/M$^2$.

11. A method of claim 1 wherein the amount of sulfuric acid is an amount producing between about 2% to about 4%, by weight, in the reaction product.

12. A method for preparation of an alkyl glycolate by carbonylation of formaldehyde, the method comprising:
    bringing together in a reaction zone an aqueous formaldehyde concentrate comprising between about 60% by weight and about 85% by weight formaldehyde, carbon monoxide and a catalytic amount of sulfuric acid, in the absence of an effective amount of added Group IB cocatalyst, the carbon monoxide partial pressure in said reaction zone being not greater than about $1.73 \times 10^7$ N/M$^2$, thereby effecting a reaction producing a carbonylation reaction mixture comprising in the range of from about 2% to about 10% by weight sulfuric acid and a mixture of polyglycolides having the formula:

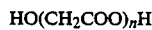
    HO(CH$_2$COO)$_n$H wherein n is an integer of at least 1,
    esterifying the polyglycolides contained in said carbonylation reaction, mixture without prior removal of the sulfuric acid, with an alcohol of the formula ROH to form an esterification product comprising an alkyl glycolate of the formula $$\text{HO}-\underset{\underset{\text{H}}{|}}{\overset{\overset{\text{H}}{|}}{\text{C}}}-\overset{\overset{\text{O}}{\|}}{\text{C}}-\text{OR}$$

wherein R is lower alkyl.

13. A method as set forth in claim 12 wherein said carbonylation reaction mixture comprises between about 2% by weight and about 4% by weight sulfuric acid.

14. A method as set forth in claim 12 wherein the temperature in said reaction zone is between about 150° C. and about 180° C.

15. A method of claim 12 wherein the lower alkyl group is methyl.

16. A method as set forth in claim 12 further including the step of adding a base to said esterification product to produce a treated product comprising an alkyl glycolate and a precipitate.

17. A method as set forth in claim 16 wherein said precipitate is removed from said treated product by filtration, thereby producing a filtrate comprising said alkyl glycolate.

18. A method as set forth in claim 17, further comprising separating said alkyl glycolate from the filtrate.

19. A method as set forth in claim 18 wherein said alkyl glycolate is separated from the filtrate by distillation.

20. A method as set forth in claim 19 wherein said alkyl group is methyl.

21. A method as set forth in claim 12 wherein the formaldehyde conversion is at least about 90%.

22. A method as set forth in claim 21 wherein the selectivity to polyglycolide is at least about 85% based upon the formaldehyde converted.

23. A method as set forth in claim 12 wherein the concentration of formaldehyde in said aqueous formaldehyde concentrate is between about 70% by weight and about 80% by weight.

24. A method of claim 12 wherein the pressure is in the range of from about $5.5 \times 10^6$ N/M$^2$ to about $1.38 \times 10^7$ N/M$^2$.

25. A method as set forth in claim 12 wherein the yield of polyglycolide is at least about 85 mole percent based on formaldehyde input.

26. A method as set forth in claim 12 wherein the reaction time is in the range of from about 2 to about 10 hours.

27. A method as set forth in claim 12 wherein the carbonylation reaction is a continuous process.

28. A method of claim 27 wherein the reaction time is within the range of from about 2 to about 20 hours.

* * * * *